US011458202B2

(12) United States Patent
Gil Vasconcelos Mota et al.

(10) Patent No.: US 11,458,202 B2
(45) Date of Patent: Oct. 4, 2022

(54) CYANOBACTERIUM EXTRACELLULAR POLYMER, COMPOSITIONS AND USES THEREOF

(71) Applicants: INSTITUTO DE BIOLOGIA MOLECULAR E CELULAR—IBMC, Oporto (PT); UNIVERSIDADE DO PORTO, Oporto (PT)

(72) Inventors: Rita Gil Vasconcelos Mota, Oporto (PT); Paula Tamagnini, Matosinhos (PT); Luis Miguel Gales Pereira Pinto, Oporto (PT); José Pedro Santos Leite, Leça de Palmeira (PT); Sara Isabel Macedo Bernardes Pereira, Oporto (PT)

(73) Assignee: INSTITUTO DE BIOLOGIA MOLECULAR E CELULAR—IBMC, Oporto (PT)

( * ) Notice: Subject to any disclaimer, the term of this patent is extended or adjusted under 35 U.S.C. 154(b) by 0 days.

(21) Appl. No.: 17/019,991

(22) Filed: Sep. 14, 2020

(65) Prior Publication Data

US 2021/0093722 A1  Apr. 1, 2021

Related U.S. Application Data

(63) Continuation of application No. 16/329,906, filed as application No. PCT/IB2017/055263 on Sep. 1, 2017, now abandoned.

(30) Foreign Application Priority Data

Sep. 1, 2016 (PT) ........................ 109604

(51) Int. Cl.
| | | |
|---|---|---|
| *A61K 47/36* | (2006.01) | |
| *A61K 8/73* | (2006.01) | |
| *A61Q 19/08* | (2006.01) | |
| *A61K 9/00* | (2006.01) | |
| *A61Q 19/00* | (2006.01) | |
| *A61K 9/08* | (2006.01) | |
| *A61P 17/02* | (2006.01) | |
| *A61K 8/04* | (2006.01) | |
| *A61K 8/64* | (2006.01) | |
| *A61K 9/06* | (2006.01) | |
| *A61K 45/06* | (2006.01) | |

(52) U.S. Cl.
CPC .............. *A61K 47/36* (2013.01); *A61K 8/042* (2013.01); *A61K 8/64* (2013.01); *A61K 8/73* (2013.01); *A61K 9/0014* (2013.01); *A61K 9/0019* (2013.01); *A61K 9/0053* (2013.01); *A61K 9/06* (2013.01); *A61K 9/08* (2013.01); *A61K 45/06* (2013.01); *A61P 17/02* (2018.01); *A61Q 19/00* (2013.01); *A61Q 19/08* (2013.01)

(58) Field of Classification Search
CPC ............ A61K 47/36; A61K 8/042; A61K 8/64
See application file for complete search history.

(56) References Cited

U.S. PATENT DOCUMENTS

| | | | |
|---|---|---|---|
| 8,277,849 B2 | 10/2012 | Dillon et al. | |
| 2007/0167397 A1 | 7/2007 | Dillon et al. | |
| 2007/0167398 A1* | 7/2007 | Dillon ................. | A23K 10/30 514/54 |
| 2009/0069213 A1* | 3/2009 | Avila ................. | A61K 8/9722 514/1.1 |
| 2015/0344848 A1 | 12/2015 | Senni et al. | |

FOREIGN PATENT DOCUMENTS

| | | |
|---|---|---|
| CN | 105 169 488 | 12/2015 |
| CN | 105 199 740 | 12/2015 |
| EP | 2376638 | 10/2011 |
| WO | 2015069634 | 5/2015 |

OTHER PUBLICATIONS

Liu, Liwei, et al. "P189: Nostoginosins, potential trypsin inhibitors discovered from *Nostoc* sp. strain FSN," 2012 International Symposium on Phototrophic Prokaryotes.
Pereira, Sara, et al. "Complexity of cyanobacterial exopolysaccharides: composition, structures, inducing factors and putative genes involved in their biosynthesis and assembly." FEMS microbiology reviews 33.5 (2009): 917-941.
Parikh, Amit, and Datta Madamwar. "Partial characterization of extracellular polysaccharides from cyanobacteria" Bioresource Technology 97.15 (2006): 1822-1827.
Mota, Rita, et al. "Production and characterization of extracellular carbohydrate polymer from *Cyanothece* sp. CCY 0110." Carbohydrate polymers 92.2 (2013): 1408-1415.
Mota, Rita, et al. "Released polysaccharides (RPS) from *Cyanothece* sp. CCY 0110 as biosorbent for heavy metals bioremediation: interactions between metals and RPS binding sites." Applied microbiology and biotechnology 100.17 (2016): 7765-7775.
Shah, Vishal, et al. "Characterization of the extracellular polysaccharide produced by a marine cyanobacterium, *Cyanothece* sp. ATCC 51142, and its exploitation toward metal removal from solutions." Current Microbiology 40.4 (2000): 274-278.
Shah, Vishal, Nikki Garg, and Datta Madamwar. "Exopolysaccharide production by a marine cyanobacterium *Cyanothece* sp." Applied biochemistry and biotechnology 82.2 (1999): 81-90.
Database WPI, 0, Derwent World Patents Index, vol. 2016, No. 12, Database accession No. 2016-02894x, XP002776185 & CN105199740 A 20151230 [X] 27 * abstract *.

(Continued)

*Primary Examiner* — Pancham Bakshi
(74) *Attorney, Agent, or Firm* — Leason Ellis LLP

(57) ABSTRACT

The polysaccharide released from the unicellular cyanobacterium *Cyanothece* sp. CCY 0110 exhibits low cytotoxicity and proves to be suitable for the delivery of macromolecules. The cyanobacterium extracellular polymer disclosed in the present subject-matter, namely a polysaccharide and more in particular an heteropolysaccharide, assembles with proteins into a new phase with gel-like behaviour and the release kinetics can be modulated (i.e., delayed) by adding divalent cations and/or also exhibits physical and chemical properties typical of a bioemulsifier or a bioflocculant.

12 Claims, 8 Drawing Sheets

(56) References Cited

OTHER PUBLICATIONS

Database WPI, 0, Derwent World Patents Index, vol. 2016, No. 17, Database accession No. 2016-030604, XP002776186 & CN105169488 A 20151223 (Univ Beihang) [X] 24 * abstract *.

Appel EA, Loh XJ, Jones ST, Dreiss CA, Scherman OA. 2012. Sustained release of proteins from high water content supramolecular polymer hydrogels. Biomaterials 33(18):4646-52.

Ahmed TA, Aljaeid BM. 2016. Preparation, characterization, and potential application of chitosan, chitosan derivatives, and chitosan metal nanoparticles in pharmaceutical drug delivery. Drug Desing, Development and Therapy 10:483-507.

Pereira S, Zille A, Micheletti E, Moradas-Ferreira P, De Philippis R, Tamagnini P. 2009. Complexity of cyanobacterial exopolysaccharides: Composition, structures, inducing factors and putative genes involved in their biosynthesis and assembly. FEMS Microbiology Reviews 33(5):917-941.

Mota R, Guimarães R, Büttel Z, Rossi F, Colica G, Silva CJ, Santos C, Gales L, Zille A, De Philippis R and others. 2013. Production and characterization of extracellular carbohydrate polymer from *Cyanothece* sp. CCY 0110. Carbohydrate Polymers 92(2):1408-1415.

Koutsopoulos S, Unsworth LD, Nagai Y, Zhang S. 2009. Controlled release of functional proteins through designer self-assembling peptide nanofiber hydrogel scaffold. Proceedings of the National Academy of Sciences 106(12):4623-4628.

Manivasagan M. et al, "Marine polysaccharide-based nanomaterials as a novel source of nanobiotechnological applications" Internacional Journal of Biological Macromolecules 82(2016) 315-327 Oct. 30, 2015.

Colzi I. et al, "Antibiotic delivery by liposomes from prokaryotic microorganisms: similia cum similis works better" European Journal of Pharmaceutics and Biopharmaceutics 94 (2015) 411-418 Jun. 25, 2015.

Mota R. et al, "Production and characterization of extracellular carbohydrate polymer from *Cyanothece* sp. CCY 0110" carbohydrate polymer 93 (2013)1408-1415 Nov. 3, 2012.

J. Mareš et al., "Taxonomic resolution of the genus *Cyanothece* (Chroococcales, Cyanobacteria), with a treatment on Gloeothece and three new genera, *Crocosphaera*, *Rippkaea* and *Zehria*", Journal of phycology, Apr. 2019.

\* cited by examiner

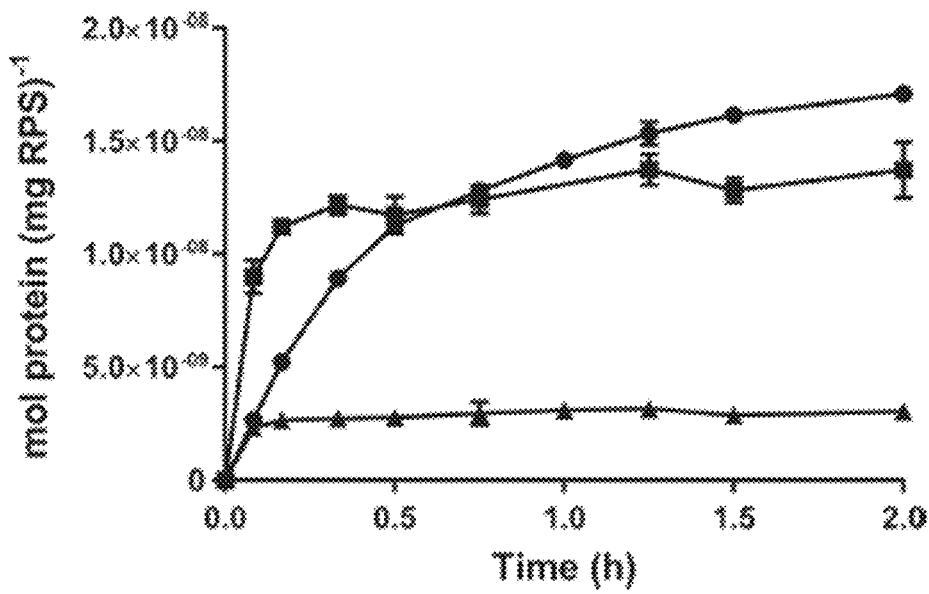
Fig. 3
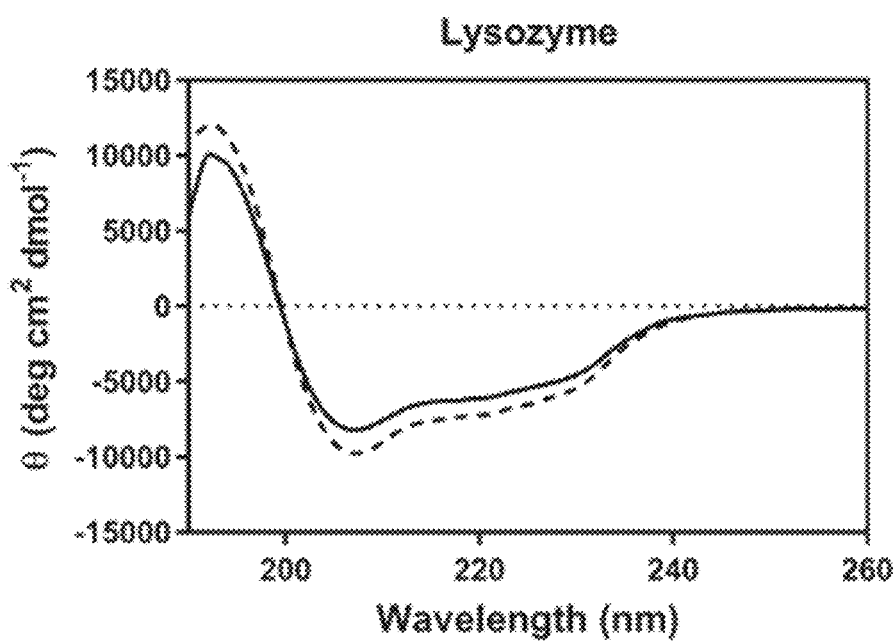
Fig. 4.1

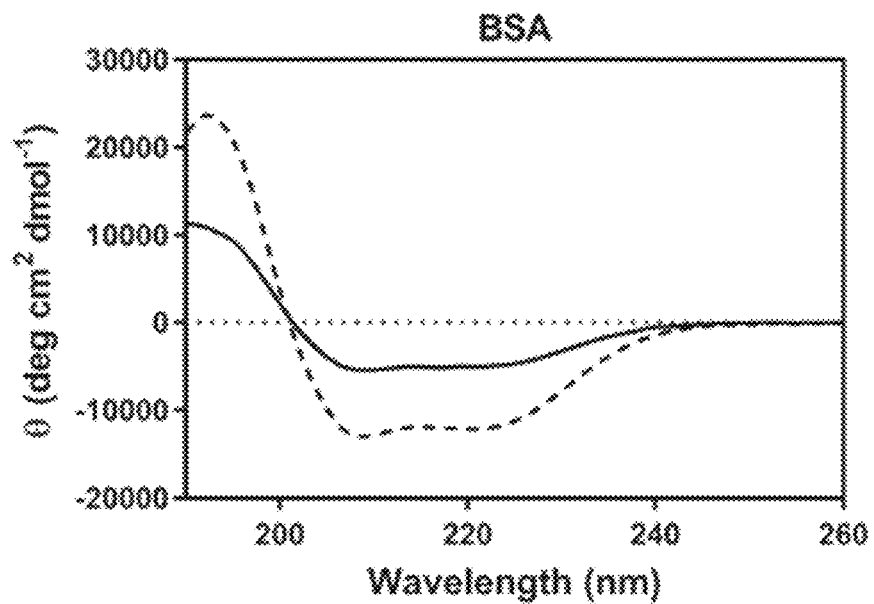
Fig. 4.2
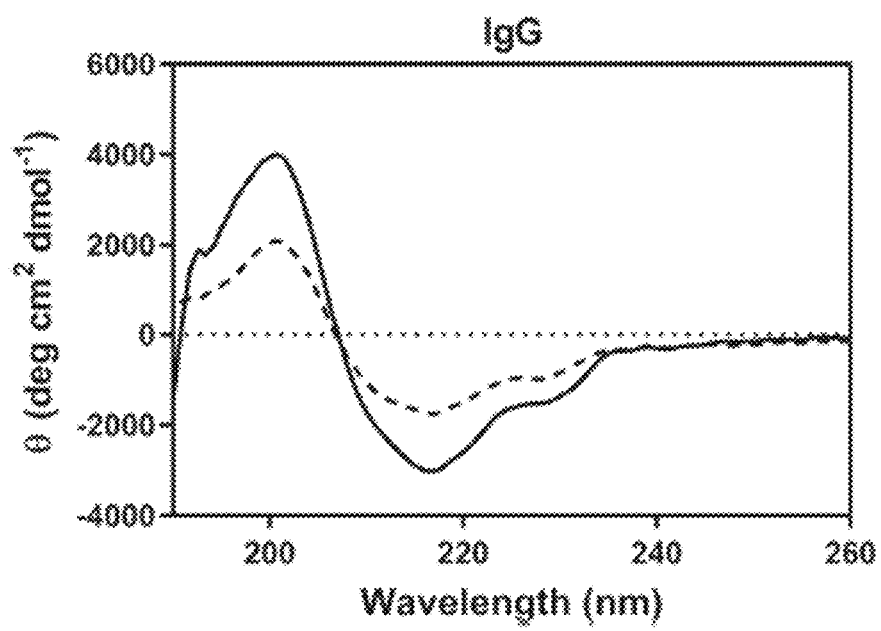
Fig. 4.3

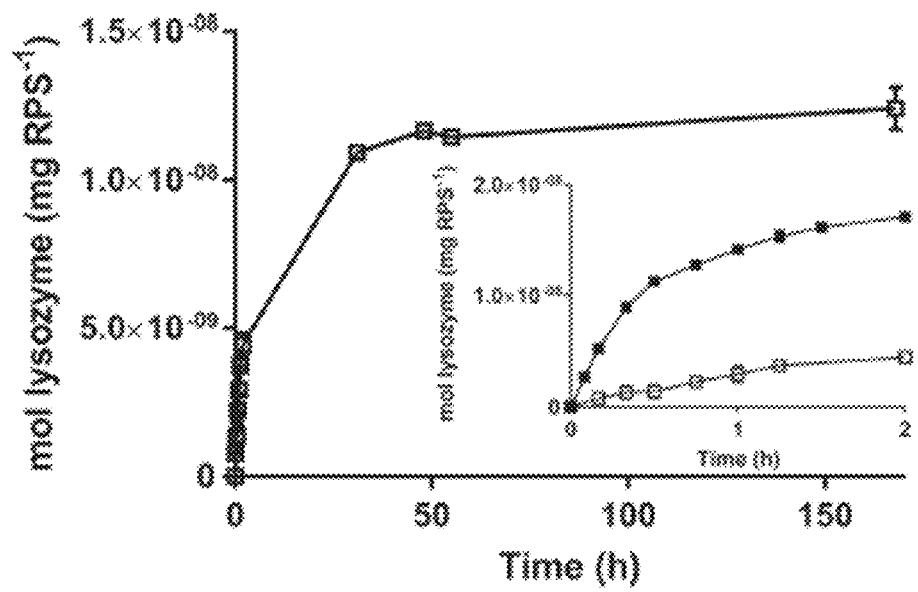
Fig. 5
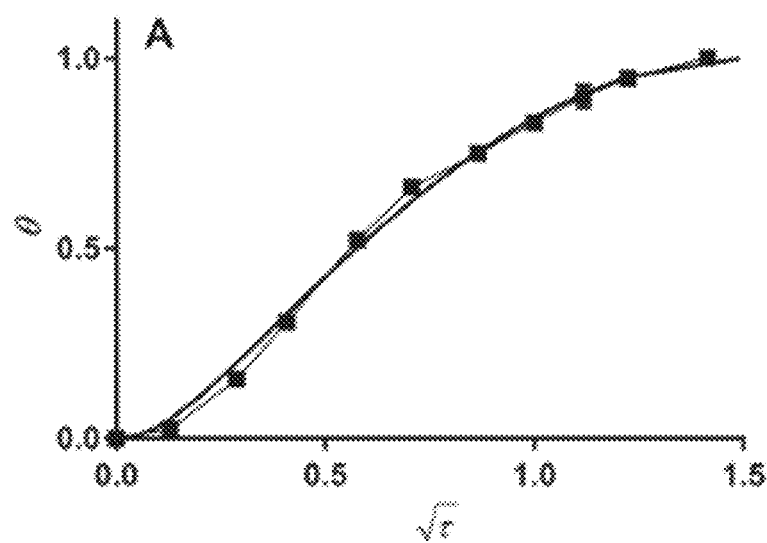
Fig. 6-A

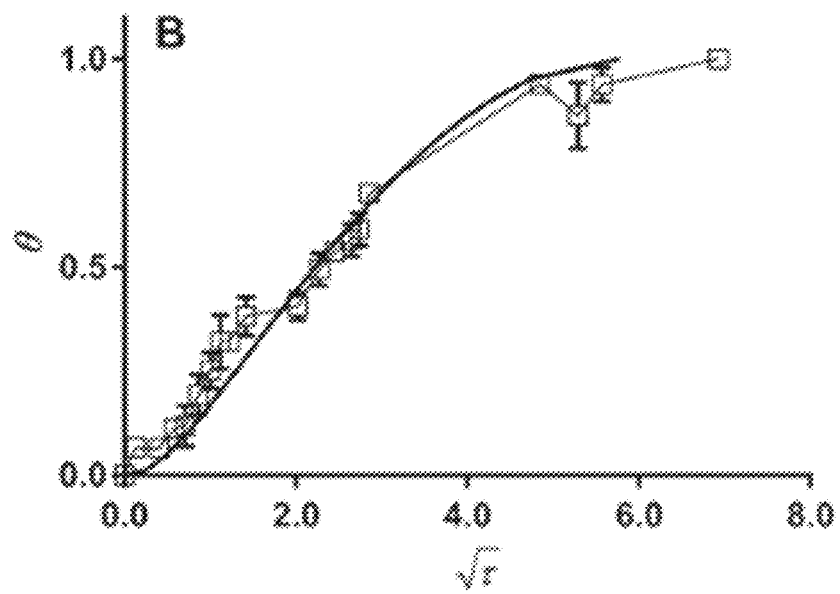
Fig. 6-B
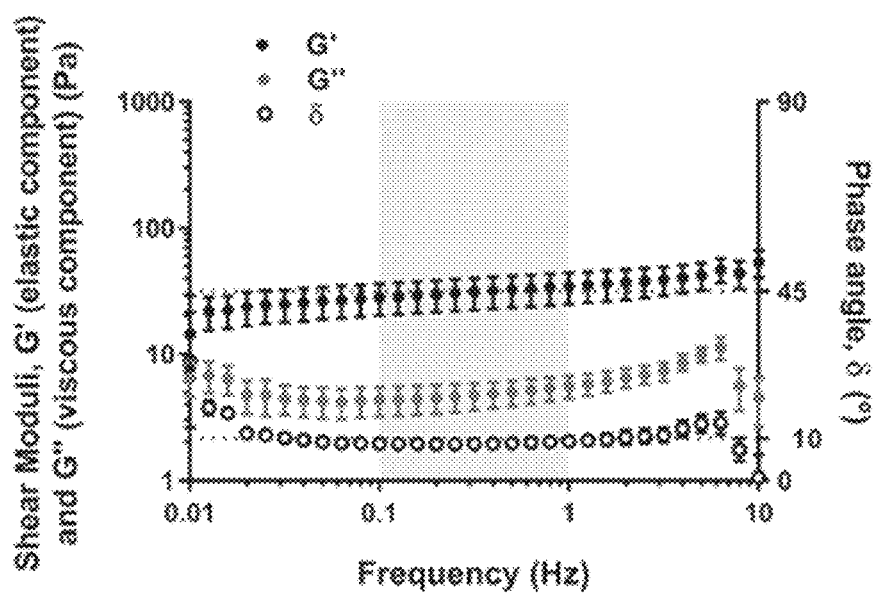
Fig. 7-A

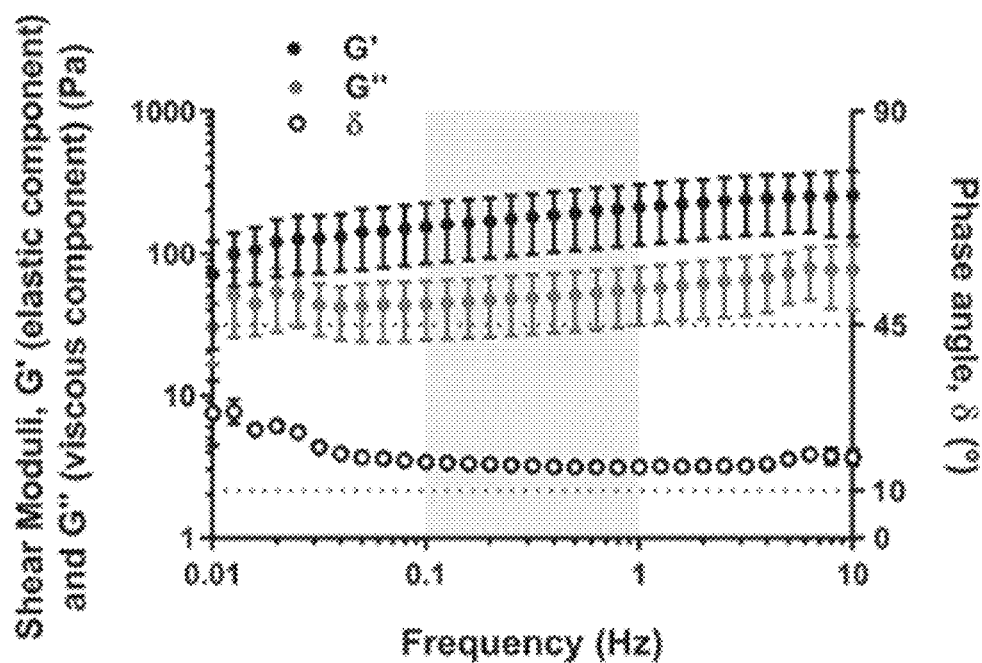
Fig. 7-B
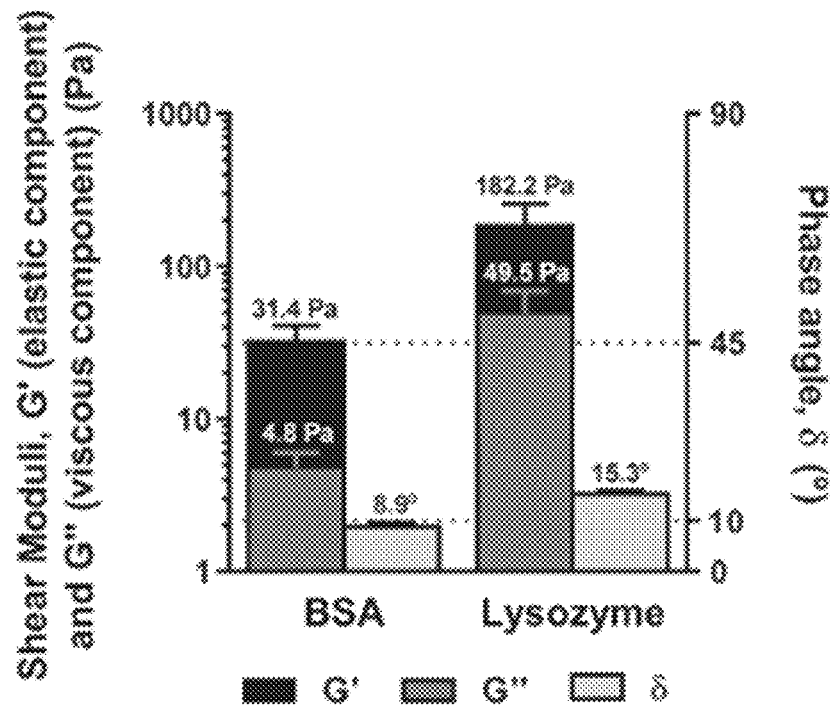
Fig. 7-C

CYANOBACTERIUM EXTRACELLULAR POLYMER, COMPOSITIONS AND USES THEREOF

CROSS-REFERENCE TO RELATED PATENT APPLICATIONS

This application is Continuation of U.S. patent application Ser. No. 16/329,906 filed Mar. 1, 2019, which is a U.S. National Phase Application under 35 U.S.C. § 371 of International Patent Application No. PCT/IB2017/055263, filed Sep. 1, 2017, and claims priority to Portuguese Patent Application no. 109604, filed Sep. 1, 2016, all of which are hereby incorporated by reference in their respective entireties.

TECHNICAL DOMAIN

The polysaccharide released from the unicellular cyanobacterium *Cyanothece* sp. CCY 0110 exhibits low cytotoxicity and proves to be suitable for the delivery of macromolecules.

The cyanobacterium extracellular polymer disclosed in the present subject-matter, namely a polysaccharide and more in particular an heteropolysaccharide, assembles with proteins into a new phase with gel-like behaviour and the release kinetics can be modulated (i.e., delayed) by adding divalent cations and/or also exhibits physical and chemical properties typical of a bioemulsifier or a bioflocculant.

BACKGROUND ART

Natural polymers present advantages over those of chemical synthetic origin, due to their biodegradability, biocompatibility and apparent lack of toxicity.

The physical and chemical characteristics of the polymer, such as water binding capacity, rheology, high molecular weight, complex molecular structure, and the possibility of being chemically modified, enable to present diverse functional properties, such as thickening, texturizing, gelling, emulsion stabilizing, flocculating, and nano/microstructures production abilities. Polymers with high molecular weight generally present high viscosity, tensile strength and resistance to shear, which are important characteristics for industrial applications, in particular in food industry, for providing good sensory qualities, flavour release and suspending properties in the production of cake mixes, salad dressings, sauces, puddings and dairy products for example, and in cosmetic industry, for the production of lotions, creams and gels.

In clinical therapy, chemically synthesized small-molecule drugs are still the main class of prescribed therapeutic agents. However, proteins have been gathering a lot of attention, due to some of their practical and financial advantages over small drugs. They possess high specificity for biological processes and present less risk of severe adverse effects (a consequence of the aforementioned high specificity), as well as, in most cases, less risk of triggering an immune response. In addition, they are more rapidly approved by authorities, like the FDA, and they are more easily patentable, making them much more attractive for big investment in R&D. Despite all these, the use of therapeutic proteins is not well established. Their stability and solubility, routes of administration and elimination, great susceptibility to free circulating proteases (which diminishes their half-life) and, in some cases, triggering of immune responses (e.g., when using antibodies) are all potential obstacles that justify why small drugs are still more predominately used. In this regard, the use of a scaffold in conjunction with the protein solves most, if not all, of the previously mentioned caveats. Traditionally, hydrogels are very appealing for drug delivery applications due to the high water content, biocompatibility, and the ease of synthesis.[1] Their porous structure can be tuned for the delivery of a wide size range of molecules by controlling the density of cross-links in the gel matrix.[1]

Naturally occurring polysaccharides are among the most used polymers in the preparation of hydrogels. Chitosan, the second most abundant polysaccharide in nature, is the most widely studied naturally derived polymer in drug delivery for small drugs or macromolecules.[2] Others, like algae-derived alginate, have been used as a matrix for the entrapment and/or delivery of biomolecules like DNA, proteins, vitamins, and cells, depending on the thickening, gel-forming, and stabilizing properties. However, their use in clinic is not widespread, due to some drawbacks, such as long-term exposure toxicity, poor bioavailability of the active principles (i.e., low release rate), and possible immunogenicity.[2] In that regard, other alternatives are emerging, for example, the extracellular polymeric substances (EPS) produced and secreted by microorganisms. These polymers are more easily and affordably obtainable, with dextran being the hallmark of EPS used in pharmaceutical industry as a plasma expander. Sulfated microbial polymers have been studied as site-specific drug carriers, due to their intrinsic biocompatibility and potential low cost. Other microbial polymers were shown to provide improved site specificity and meet the desired therapeutic needs for colonic diseases[13] or liver-specific diseases.

Among microbial EPS, the polymers derived from cyanobacteria have particular features that stand out such as high content in sulfate groups and the presence of one or two uronic acids that contribute to their strong anionic character.[3] *Cyanothece* sp. CCY 0110 is a marine $N_2$-fixing unicellular cyanobacterium isolated from coastal waters of Zanzibar that is among the most efficient producers, releasing most of the polymer to the culture medium (RPS), facilitating its recovery. An extensive characterization of this polymer showed that, in agreement to what was previously described for other cyanobacterial polymers, *Cyanothece*'s RPS are complex macromolecules, composed of nine different monosaccharides including two uronic acids, peptides, and sulfate groups. In addition, they are remarkably thermostable and mainly of amorphous nature.[3] The overall anionic nature, hydrophobicity, and different possible conformations of these polymers make them very attractive for biotechnological applications, such as the removal of metal ions from waste waters. Moreover, a possible low cytotoxicity induced by the polysaccharidic content of *Cyonothece*'s RPS promotes its use as an in vivo delivery vehicle of therapeutic drugs. The present disclosure presents the first report of the use of a cyanobacteria-derived polymer for drug delivery. In this work, it was investigated the release kinetics of small molecule drugs and proteins from the *Cyanothece* extracellular polymer. A release mathematical model is proposed and the biocompatibility of RPS from *Cyanothece* was assessed in vitro using human dermal neonatal fibroblasts.

These facts are disclosed in order to illustrate the technical problem addressed by the present disclosure.

GENERAL DESCRIPTION

The unicellular cyanobacterium *Cyanothece* sp. CCY 0110 is a highly efficient producer of extracellular polymeric substances, releasing up to 75% of the polymer to the culture medium. The carbohydrate polymer released to the medium (RPS) was previously isolated and characterized; it is composed of nine different monosaccharides including two uronic acids, and also containing peptides and sulfate groups.

The present disclosure shows that the RPS spontaneously assembles with proteins at high concentrations leading to a phase transition. The proteins are released progressively and structurally intact near physiological conditions, primarily through the swelling of the polymer-protein matrix. The releasing kinetics of the proteins can be modulated through the addition of divalent cations, such as calcium. Notably, the polymer is not toxic to human dermal neonatal fibroblasts in vitro at RPS concentrations bellow 0.1 mg mL$^{-1}$. The results show that this polymer is a good candidate for the delivery of therapeutic macromolecules.

As an alternative to the traditional clinical practice of administering non-specific drugs, an interest in shifting to more directed treatments is growing. In that regard, proteins are excellent candidates, as they are highly specialized agents with multiple functions, like transport and catalysis. However, some of their features turn into drawbacks when talking about human administration; for example, low circulating stability and/or solubility and possible triggering of immune responses. To avoid these problems, scaffolds are an excellent option, as the widespread and natural-derived hydrogel-based polysaccharides chitosan and alginate. Nevertheless, they might trigger immune responses and lead to long-term exposure toxicity problems.

The present disclosure relates to the use of a released polysaccharidic polymer (RPS) produced by the unicellular cyanobacterium *Cyanothece* sp. CCY 0110 as an alternative to the currently available scaffolds. This cyanobacterial strain not only has the usual low requirements for culture maintenance, but also produces high amounts of polymer, easy to extract and recover. All these features make this RPS very attractive, in particular from an economic point of view.

An aspect of the present disclosure relates to polysaccharide released from *Cyanothece* sp. CCY 0110 for use in medicine, pharmaceutical, cosmetic or food industry.

*Cyanothece* sp. CCY 0110 is a diazotrophic single cell cyanobacterium. The cells can be ovals or cylindrical and can be found in groups. *Cyanothece* sp. CCY 0110 can be order in the Culture Collection of Yerseke, The Netherlands. (Isolated from: Chwaka, Zanzibar. Type of sample: sediment. Incubation T°: 23° C. SSU RRNA SEQUENCE: max identity 99% *Cyanothece* sp. ATCC 51142, 1326 bp).

In an embodiment the polysaccharide disclosed in the present subject-matter comprises mannose, glucose, galactose, xylose, arabinose, rhamnose, fucose, galacturonic and glucuronic acids and peptides.

In an embodiment the polysaccharide disclosed in the present subject-matter may be use as a drug delivery vehicle, in particular wherein a protein delivery vehicle.

In an embodiment the polysaccharide disclosed in the present subject-matter may comprise a divalent cation selected from the following list: $Ba^{2+}$, $Fe^{2+}$, $Ca^{2+}$, $Cu^{2+}$, $Zn^{2+}$, and mixtures thereof, preferably $Ca^{2+}$.

In an embodiment the polysaccharide disclosed in the present subject-matter may be use in the treatment or prevention of a wound, mucous or skin infection disease, inflammatory or allergic condition, lipodermatosclerosis, skin injures, skin aging disease or dysfunction, bone or cartilage tissue damage.

In an embodiment the polysaccharide disclosed in the present subject-matter may be use in the treatment or prevention of wounds. Namely wherein the wound is an open wound, acute wound, chronic wound, infected wound or surgical wound; preferably ulcer of venous, arterial aetiology, mixed aetiology, decubitus ulcer, diabetic ulcer, and combinations thereof.

In an embodiment the polysaccharide disclosed in the present subject-matter may have a weight of the polysaccharide vary between 1500-5000 KDa.

In an embodiment the polysaccharide disclosed in the present subject-matter may be use in the treatment or prevention of mucous and skin infection disease. Namely wherein the mucous and skin infection diseases are selected from the following list: mucositis, gingivitis, periodontitis, vaginitis, anal fissure, skin ulcer, otitis, dermatoses, and combinations thereof; and skin aging is selected from the following list: wrinkles, expression wrinkles, stretch marks, skin photoaging, and combinations thereof.

In an embodiment the polysaccharide disclosed in the present subject-matter may be use in the treatment or prevention of the inflammatory or allergic conditions, and can be selected from the following list: dermatitis, atopic dermatitis, allergic dermatitis, seborrheic dermatitis, and combinations thereof.

In an embodiment the polysaccharide disclosed in the present subject-matter may be topically administered to a subject once a day, twice a day, or three times a day.

In an embodiment the polysaccharide disclosed in the present subject-matter may be parenterally administered to a subject once a day, twice a day, or three times a day.

In an embodiment the polysaccharide disclosed in the present subject-matter may be orally administered to a subject once a day, twice a day, or three times a day.

Another aspect of the present invention relates to a pharmaceutical composition comprising the polysaccharide disclosed in the present subject-matter for use in medicine or cosmetic.

In an embodiment the composition may comprise 0.01-2% (w/v) of polysaccharide; preferably 0.05-1% (w/v) of polysaccharide; more preferably 0.1-0.5% (w/v) of polysaccharide.

In an embodiment the composition may comprise a further polysaccharide, preferably the additional polysaccharide may be selected from the following list: cellulose; alginate; chitosan, gellan gum, arabic gum, dextrin, dextran, collagen, guar gum, carrageenan, xanthan gum, hyaluronic acid, mixtures thereof.

In an embodiment the active ingredient is: a protein, a drug, an anti-inflammatory agent, an antiseptic agent, an antipyretic agent, an anaesthetic agent, an anti-cancer agent, a therapeutic agent, or mixtures thereof.

In an embodiment the composition may be in a topical form, or an injectable form, or an oral form.

In an embodiment the topical composition may be in a gel, or a cream, or a lotion.

The composition of the present disclosure may further comprise a hydrogel or a plurality of hydrogels.

In an embodiment the composition may have a hydrogel selected from a list consisting of carbopol, matrigel, hyaluronic acid, dextran, alginate, collagen, gellan gum, or mixtures thereof.

Another aspect of the present invention relates to scaffold for the use in medicine comprising the polysaccharide disclosed in the present subject-matter.

Another aspect of the present invention relates to a viscosupplement for the use in medicine comprising the polysaccharide disclosed in the present subject-matter.

Another aspect of the present invention relates to the use of a polysaccharide as an emulsifier, or an emollient, or a gelling agent, or a lubricant, or a thickener for parenteral compositions, or a flocculant, or an encapsulating agent, or an ocular agent, or an anti-wrinkle agent, or a skin care agent or a hydrogel.

Another aspect of the present invention relates to the use of a polysaccharide as skin care agent comprising a firming agent, an anti-stretch mark agent, a conditioner, a skin relaxant agent.

A wound is a type of injury which happens relatively quickly in which skin is torn, cut, or punctured (an open wound), or where blunt force trauma causes a contusion (a closed wound). In pathology, it specifically refers to a sharp injury, which damages the dermis of the skin.

The polysaccharide of the present disclosure has the following features: is composed by nine different monosaccharides (mannose, glucose, galactose, xylose, arabinose, rhamnose, fucose, galacturonic and glucuronic acids), peptides and sulfate groups; is amorphous and has high molecular weight and high thermal stability.

The present disclosure delays macromolecule release kinetics by adding calcium to the polymer-macromolecular complex. The polymeric scaffold was proven to be inert and did not interfere with the active principle (i.e. proteins). Finally, it was assessed that the polymer forms a soft-gel structure when in contact with proteins, such as lysozyme or bovine serum albumin. This feature may lead to even further applications, like a three-component system for drug delivery or a matrix for in vitro cell cultures.

Throughout the description and claims the word "comprise" and variations of the word, are not intended to exclude other technical features, additives, components, or steps. Additional objectives, advantages and features of the solution will become apparent to those skilled in the art upon examination of the description or may be learned by practice of the solution.

BRIEF DESCRIPTION OF THE DRAWINGS

The following figures provide preferred embodiments for illustrating the description and should not be seen as limiting the scope of disclosure.

FIG. 3: Release profiles of BSA (■), lysozyme (●), and IgG (▲) from *Cyonothece's* RPS.

FIGS. 4.1-4.3: Far-UV CD spectra of released (solid line) protein solutions from the RPS hydrogel and of the correspondent freshly prepared protein samples (broken line).

FIG. 5: Release profile of lysozyme from RPS after associative phase preparation in the presence of 0.1 M $CaCl_2$. Inset: initial release profile of lysozyme loaded into RPS in the absence (■) and presence (□) of 0.1 M $CaCl_2$.

FIG. 6 A-8: Lysozyme release from RPS: A) without $CaCl_2$ and B) with 0.1 M $CaCl_2$, plotted as a function of the square root of dimensionless time (Equation (7)). The lines represent the simulated curves (Equation (6), (A) $N_s$=8, Da=9, and Sh→∞ and (B) $N_2$=120, Da=9, and Sh→∞).

FIG. 7 A-C: Oscillatory rheometry measurements (frequency sweeps) of the RPS/SA (A) and RPS/lysozyme (8) solutions; average values of the viscoelastic data (G', G", and δ) within the region highlighted in grey (0.1-1 Hz) (C).

DETAILED DESCRIPTION

Release of therapeutic molecules from *Cyonothece* sp. CCY 0110 RPS. Small molecule drugs are the most common therapeutic agents, and thus the potential of the isolated cyanobacterial extracellular polymer (RPS) as a controlled drug delivery system was evaluated with a small positively charged antiarrhythmic drug, procainamide.

Figure 2:
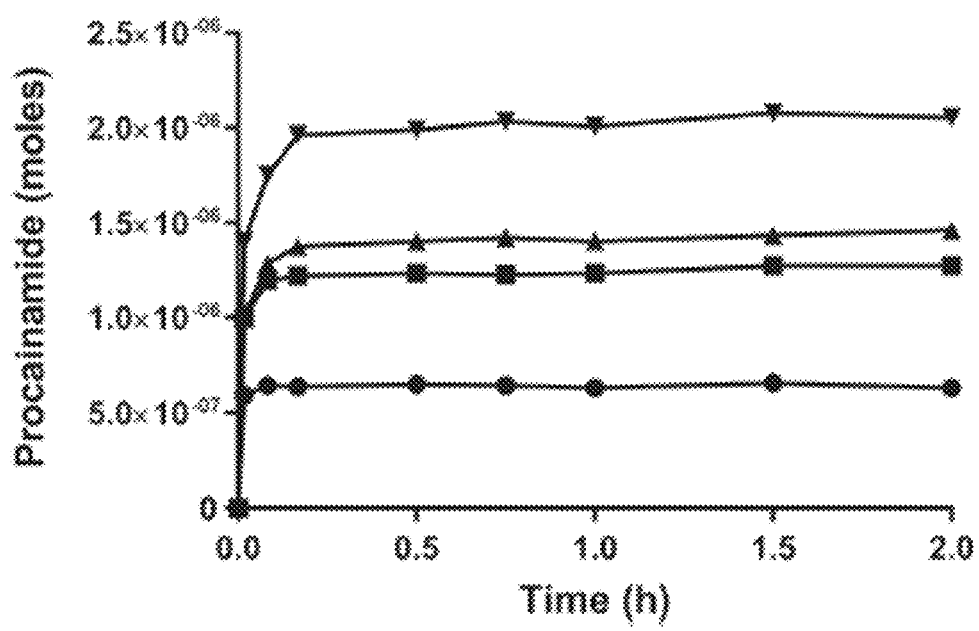
FIG. 2: Procainamide release profiles from *Cyanothece* sp. CCY 0110 RPS at different polymer concentrations: 3.5 (▼), 1.9 (▲), 1.1 (■), and 0.4 (●) mg mL$^{-1}$.

Despite the significant drug loading (≈0.4 mg of procainamide per mg of RPS), probably due to the electrostatic interactions between drug and polymer, procainamide is readily released in few minutes (FIG. 2). Moreover, the increase in the polymer concentration has a negligible effect in the retardation of drug release.

Subsequently, the loading and release of macromolecules from RPS was investigated. The properties of the three proteins used (lysozyme, BSA, and IgG) are summarized in Table 1. According to the isoelectric points (pI), BSA is negatively charged at pH 7.4, the physiological mimicking pH value at which the release experiments were performed using 1×PBS. Lysozyme, on the other hand, carries a net positive charge, while IgG is globally uncharged. The releasing profiles of the three proteins are shown in FIG. 3. IgG is the least incorporated in the polymer matrix and there is a considerable burst release effect observable for BSA and IgG. The surface net charges of BSA (negative) and of IgG (neutral) do not favour the formation of strong electrostatic interactions with the negatively charged polymer and thus the BSA and IgG molecules most probably remain very mobile in the polymer framework diffusing rapidly toward the bulk solution. On the other hand, lysozyme which is positively charged, presumably establishes net charge interactions with RPS, being progressively released (FIG. 3). Additionally experiments with lysozyme were performed at tumour-mimicking pH of 6.0. At this pH, the lysozyme loading is smaller and the release kinetics faster. The lower pH (compared to the physiological pH 7.4) contributes to a decrease in the overall anionic charge of the polymer, explaining the reduced affinity toward positive charged molecules like lysozyme.

The ability of a protein to diffuse through a polymer phase depends upon the protein molecular size and shape. Smaller proteins diffuse faster and, in that sense, lysozyme, BSA, and IgG should be released in this order. However, the experimental results show that the release kinetics of proteins from RPS depends primarily on surface net charge of the protein, rather than on the protein molecular size, being the polymer more suitable for the progressive delivery of positively charged macromolecules.

For therapeutic proteins, it is critical that they maintain their native conformation upon RPS delivery. Very strong protein-polymer interaction may lead to protein denaturation, rendering the protein inactive upon release. The structural integrity of the proteins was confirmed by far-UV CD spectra. FIG. 4 shows that the three proteins maintained the native fold upon contact with RPS.

In an embodiment, the control of the protein release from RPS through addition of divalent cations like calcium, have the ability to bridge the negatively charged RPS polymeric chains, reducing the hydrogel mesh and consequently delaying the effective diffusion of guest molecules. For instance, the presence of calcium ions in chitosan-alginate particles delayed the release of BSA and in pectinate gel beads it delayed drug release by a few hours, depending on concentration. A similar effect occurs when positive calcium ions interact with the negatively charged RPS chains. To confirm that the protein release kinetics can be modulated by $CaCl_2$, lysozyme was loaded into RPS in presence of 0.1 M of $CaCl_2$. The correspondent release profile (FIG. 5) is indeed considerably slower; the half-time protein release point was ≈7 h against the equivalent 0.6 h obtained without calcium. A possible drawback in the reduction of the hydrogel mesh—through addition of $CaCl_2$—is size-exclusion or at least a decline in the protein maximum loading. For lysozyme, at the experimental conditions used, this reduction was nearly 20%. A similar calcium-modulated release profile was obtained for BSA, which has a significant bigger molecular size than lysozyme and in this case the reduction in the protein upload was drastic.

In the line of the proposed release mathematical model, the lysozyme release profile from RPS was re-plotted in FIG. 6 as fraction of protein released θ versus √τ (τ given by Equation (7)) for theoretical analysis. The two curves (with and without the presence of $CaCl_2$) diverge from a straight line assuming a sigmoidal shape (FIG. 6), which indicates that at least one of the processes previously mentioned—external interfacial resistance and boundary ionic exchange—is not negligible. The release experiments were conducted using orbital agitation; the frequency of agitation was increased in pre-experiments until the protein releasing profiles became unperturbed.

Thus, the external interfacial resistance should be negligible and Sh→∞. The best fit of Equation (6) was obtained with $N_s=8$ and Da=9 in the case of no addition of $CaCl_2$ during the formation of the hydrogel and $N_s=120$ and Da=9 in the presence of 0.1 M $CaCl_2$. The dimensionless release time τ decreased more than 13× due to the addition of 0.1M $CaCl_2$. Thus, the diffusion rate of macromolecules through RPS is very sensible to the presence of divalent cations and can be regulated adjusting the conditions of the polymer network formation.

In an embodiment, the rheological properties of RPS/protein associative phase. When a protein comes in contact with a polysaccharide, it can result in a segregative or associative phase separation. Due to observations of mixture behaviour during drug loading and release experiments, an associative phase forms when the RPS contacts with BSA or lysozyme (IgG was not tested given its low incorporation and subsequent release in RPS, as seen in FIG. 3). The mixtures presented different structures; while the RPS/BSA mixture was more homogeneous, the RPS/lysozyme presented a clear phase separation. The viscoelastic properties of the RPS/protein solutions were assessed to verify if they underwent a sol-gel transition (δ<45°), through oscillatory rheological measurements of the mentioned solutions (FIG. 7). Despite the low shear moduli values, the average values of the elastic component of the shear modulus for both RPS/BSA and RPS/lysozyme mixtures (G' RPS/BSA≈31.4±8.8 Pa; G' RPS/lysozyme≈182.2±74.8 Pa) (in the linear region from 0.1 to 1 Hz) was higher than the viscous component of the shear modulus (G" RPS/BSA≈4.8±1.2 Pa; G" RPS/lysozyme≈49.5±19.7 Pa), indicating a predominance of a gel-like behaviour. Moreover, the relationship between them, represented by the phase angle (δ RPS/BSA≈8.9±0.9; δ RPS/lysozyme≈15.3±0.6°), not only confirms that the solutions presented a gel-like behaviour, but also that they react to shear stress as a more solid-like material (δ=≤10°). This predominant elastic behaviour of BSA/polysaccharide mixtures was previously reported for BSA/pectin (G'≈104-105 Pa) or BSA/κ-carrageenan (G'≈104-105 Pa) and may primarily result from the electrostatic interactions between the protein and the polysaccharide chains. However, the viscoelastic properties of these systems cannot be directly compared due to the specific characteristics of the protein/polymer pairs, and their distinct structures. The RPS/BSA and RPS/lysozyme mixtures present shear moduli values similar to other soft gels, for example, Matrigel (a protein-rich preparation extracted from the extracellular matrix of mouse sarcoma, G'≈80 Pa), PuraMatrix (a self-assembling hydrogel composed of repeating amino acid sequences of Arginine-Alanine-Aspartic Acid-Alanine, G'≈5 Pa), SM-A87 EPS (exopolysaccharide secreted by a deep-sea mesophilic bacterium, G'≈=1 Pa), polyacrylamide (G'≈10 Pa),[30] or Pluronic F127-g-poly(acrylic acid) (10 Pa<G'<100 Pa).

Figure 8:
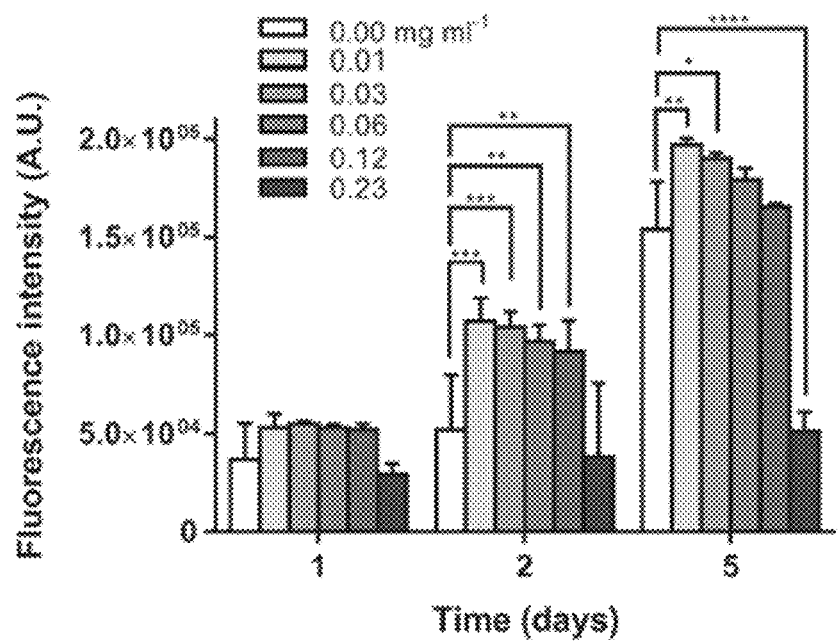
FIG. 8: Metabolic activity of fibroblasts assessed on day 1, 2, and 5 by the Resazurin assay as a function of the RPS concentration in the cellular medium (* p value ≤0.05;  p value ≤0.01; * p value ≤0.001; **** p value ≤0.0001).
Figure 9:
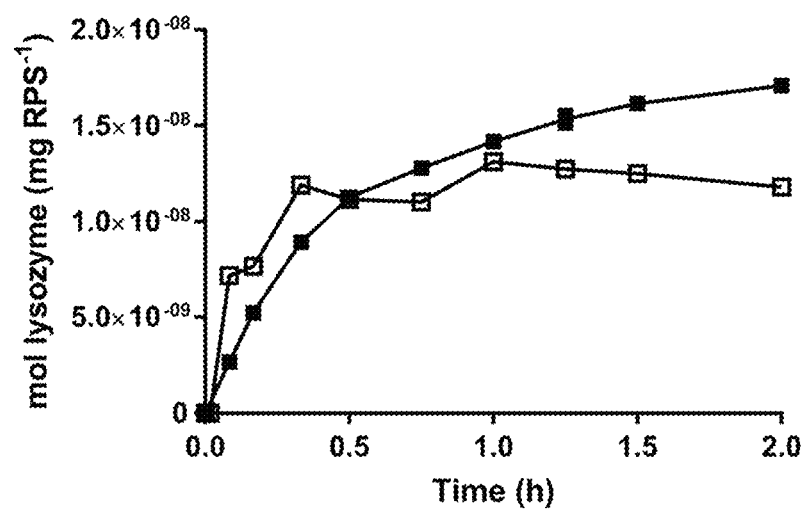
FIG. 9: Release profile of lysozyme from RPS, at physiological pH of 7.4 (■) and tumour-mimicking pH of 6.0 (□).
Figure 10:
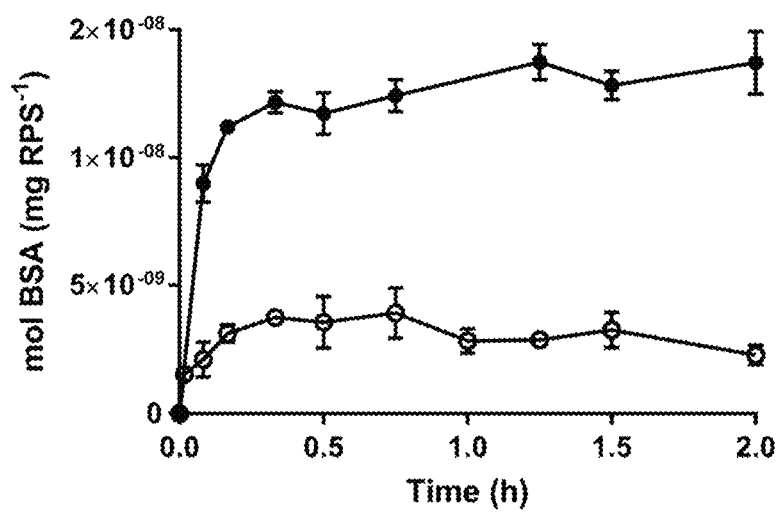
FIG. 10: Release profile of BSA from RPS after associative phase preparation in the absence (•) and presence (○) of $CaCl_2$ 0.1M.

In an embodiment, the cytotoxicity assessment of RPS was performed. Despite being a biopolymer, and thus likely being biocompatible, cytotoxicity assays are always of extreme importance. One possible usage of the RPS is the topical application of therapeutic agents. In this case, it is expected that the bulk of the polymer maintains its consistency and integrity. However, some degradation and eventual absorption of vestigial polymer molecules through the skin occurs. The metabolic activity of fibroblasts with increasing concentration of RPS, up to 0.23 mg mL$^{-1}$, was assessed by Resazurin assay at different time points (day 1, 2, and 5). The results are shown in FIG. 8. After 5 d, it is observed that 0.23 mg mL$^{-1}$ of RPS in the medium reduces the metabolic activity of fibroblast. However, at lower concentrations, RPS was not toxic to fibroblast cells and actually contributed to a slight, but statistically significant increase of metabolic activity.

In an embodiment, it was tested a polymer from a marine cyanobacterium, *Cyanothece* sp. CCY 0110, as a vehicle for drug delivery. The polymer assembles with proteins into a new phase with gel-like behaviour (as confirmed by rheological measurements), and positively charged proteins are smoothly released from the polymeric network. The release kinetics of proteins from RPS can be modulated by the addition of divalent cations, delaying release. The lysozyme release profiles from RPS present a sigmoidal shape when plotted as θ versus $t^{0.5}$. A general mathematical equation is proposed assuming a shell-progressive swelling model. The equation simulates efficiently our experimental curves and may find application in many other drug delivering systems. In addition, the polymer shows negligible cytotoxicity at the highest tested concentration on human dermal neonatal fibroblasts.

In short, this polymer is a vehicle for topical administration of therapeutic macromolecules, using the models lysozyme from chicken egg white, bovine serum albumin (BSA), and immunoglobulin G (IgG) from human serum.

In an embodiment, the RPS production and isolation was performed as follows: the unicellular cyanobacterium *Cyanothece* sp. CCY 0110 (Culture Collection of Yerseke, The Netherlands) was grown in 1 L Erlenmeyer flasks with ASNIII medium, at 25° C. under a 16 h light (30 µE m$^{-2}$ s$^{-1}$)/8 h dark regimen with aeration (1.2 L min$^{-1}$).

In an embodiment, *Cyanothece* cultures were grown until an optical density of =2.0-3.0 at 730 nm was obtained. The culture was placed in dialysis membranes (12-14 kDa of molecular weight cut-off; Medicell International Ltd., London, UK) and dialyzed against a minimum of ten volumes of deionized water for 48 h in continuous stirring. The cells were removed by centrifugation at 20 000×g for 15 min and the supernatant was precipitated with two volumes of 96% cold ethanol. The RPS was collected with sterile metal forceps, dissolved in deionized water, and precipitated once more. The collected RPS was lyophilized.

In an embodiment, small/macromolecule release experiments were conducted. Procainamide and three proteins (lysozyme, bovine serum albumin, and immunoglobulin G) were used as model molecules to study the release from RPS. The guest molecules were mixed with the RPS in ultrapure water at room temperature, as follows: procainamide at 1 mg mL$^{-1}$ and polymer at 0.4-3.5 mg mL$^{-1}$; proteins at 1:1 w/w ratio with the polymer. For determination of the release profile, the loaded RPS was isolated by centrifuging at 3000 g, 10 min and the supernatant was carefully removed. For release-triggering, 1×PBS (phosphate buffered saline) pH 7.4 or sodium phosphate 0.1 M pH 6.0 was added to a final volume of 10 mL and the sample was incubated at room temperature with orbital shaking. Time-point samples (replaced by fresh buffer) were removed for quantification by UV spectroscopy using a NanoDrop UV-vis spectrophotometer (ND-1000, NanoDrop, USA). Procainamide concentration was determined by absorption at 278 nm and protein concentration at 280 nm.

In an embodiment, circular dichroism (CD) experiments were conducted. The secondary structure of the proteins released from RPS was assessed by CD. CD spectra were recorded by a J-815 spectrometer (Jasco, Japan), equipped with a Peltier temperature control system, set at 20° C. Protein samples at 0.08-0.1 mg mL$^{-1}$, diluted in 0.1×PBS pH 7.4 were used. Spectra were recorded in a 1 mm path length quartz cell (Hellma Analytics, Germany) from 260 to 190 nm, at 50 nm min$^{-1}$, data integration time of 2 s, data-pitch 0.2 nm, and 16 accumulations per measurement. Spectra were smoothed using the Savitzky-Golay algorithm and corrected for the blank sample.

In an embodiment, rheological studies were conducted, RPS, in particular at a concentration of 5.6 mg mL$^{-1}$, was dissolved in an equally concentrated solution of BSA or lysozyme in ultrapure water, under agitation at room temperature for a week. Then, the mixtures were carefully homogenized before the assays. A rheometer (Kinexus Pro, Malvern Instruments, UK) was used to assess the viscoelastic properties of the mixtures and the oscillatory measurements were performed using parallel plates (Ø 20 mm, 0.5 mm height gap) inside the rheometer temperature-controlled hood (20° C.). First, the linear viscoelastic region (LVR) of the gels was determined by iteratively performing strain amplitude and frequency sweeps and frequency. Then, frequency sweeps (0.01-10 Hz) were performed, using a constant shear strain of 1% within the LVR, to the referred RPS/BSA mixtures (n=12) and RPS/lysozyme (n=4), to assess their viscoelastic properties—the shear modulus elastic (G') and viscous (G") components, and the phase angle (δ).

In an embodiment, biocompatibility studies were performed. Human dermal neonatal fibroblasts (ZenBio, Inc, USA) were grown in tissue culture flasks at 37° C. in a 5% $CO_2$ controlled atmosphere in Dulbecco's modified Eagle's medium (DMEM, Gibco/BRL, Gaithersburg, Md., USA) supplemented with 10% (v/v) fetal bovine serum (FBS, Gibco). Subculturing was performed by tripsinizing cultures with 0.25% trypsin (Sigma-Aldrich) and 0.05% EDTA (Sigma-Aldrich). Experiments were performed with cells at passage 9. Fibroblasts were seeded at 2.5×10$^4$ cells per well in a 24-well culture plate and incubated overnight at 37° C. and 5% $CO_2$ to allow cell adhesion. A stock solution of RPS, previously sterilized by autoclaving, was prepared in DMEM with 10% FBS at a concentration of 0.23 mg mL$^{-1}$. Cell culture medium was replaced by fresh RPS solutions at different concentrations (0, 0.01, 0.03, 0.06, 0.12, and 0.23 mg mL$^{-1}$), and metabolic activity was assessed by resazurin assay at different time points (1, 2, and 5 d). To perform the resazurin assay, the cell culture supernatant was removed for each well and cell monolayers washed with pre-warmed (37° C.) 0.1×PBS pH 7.4, followed by the addition of Resazurin solution (0.02 mg mL$^{-1}$) and incubation for 2 h at 37° C. Fluorescence was measured in triplicates in a microplate reader (Synergy MX, Biotek, USA, at Ex: 530 nm/Em: 590 nm).

In an embodiment, the protein release kinetics is controlled by phase transition, where the protein undergoes an ionic exchange-driven transition from an entrapped state in the polymer matrix to a free state in solution, where molecules rapidly diffuse. The model is based on the experimental evidence that shows that diffusion is primarily dependent on the proteins surface net charge.

Figure 1:
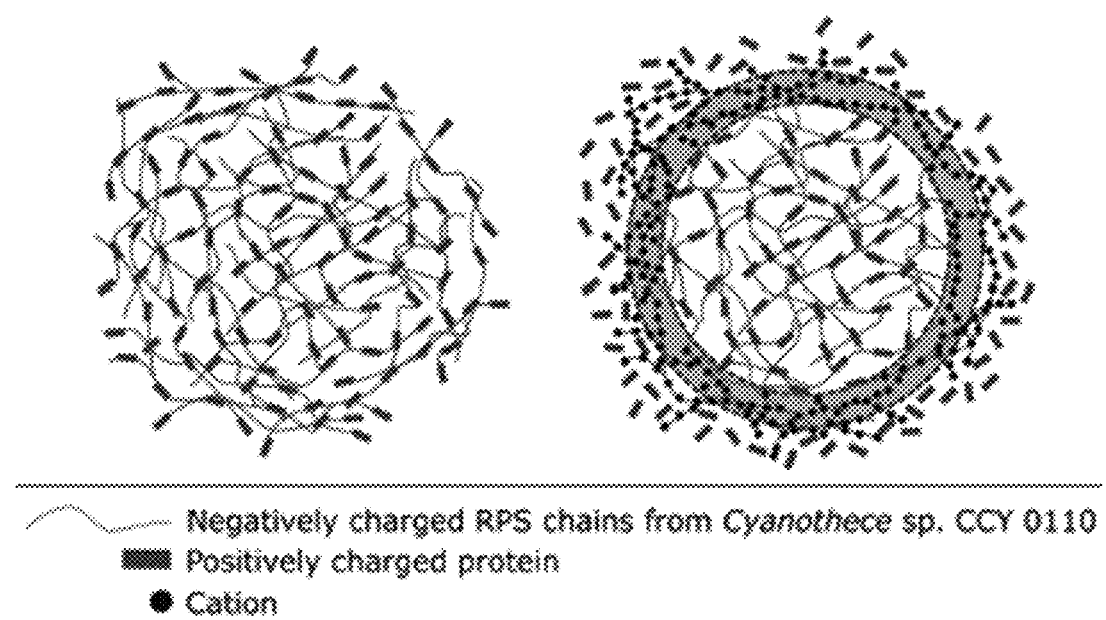
FIG. 1: Scheme of the shell-progressive ion-exchange model. RPS chains assemble with positively charged proteins into a soft solid phase (left). A cation-triggered release mechanism occurs, as a moving boundary (yellow layer), with cations replacing protein molecules in the polymeric chains. The released protein molecules rapidly diffuse to the bulk medium (right).

In an embodiment, phase transition controlled release occurs when diffusion of the guest molecules is faster than hydrogel degradation. The cations are assumed to diffuse as a moving boundary, replacing the protein molecules upon ionic interaction with the polymer matrix (FIG. 1). The total mass transfer resistance for the cations consists of the following series steps: external interfacial resistance, diffusion through the polymeric matrix, and boundary ionic exchange.

The mathematical balance of the rate of cation deposition assuming spherical particles is as follows:

$$\frac{d}{dt}\left[C_\infty \frac{4}{3}\pi(R^3 - r_c^3)\right]\rho_s = 4\pi R^2 k_l(C_l - C_s) \quad (1)$$

(external interfacial resistance)

$$= \frac{4\pi D_e}{\left(\frac{1}{r_c} - \frac{1}{R}\right)}(C_s - C_c)) \quad (2)$$

(steady diffusion through a *sperical* shell)

$$= 4\pi r_c^2 k_s C_c \quad (3)$$

(surface deposition rate at boundary)

Where R is the radius of the particle, $\rho_s$ is the density of the particle, $r_c$ is the radius of the surface boundary, $C_l$, $C_s$, and $C_c$ are the bulk fluid concentration, the particle surface concentration, and the core bounding concentration, respectively. The $C_\infty$ is the particle concentration at saturation, $k_l$ is the external interfacial mass transfer coefficient, $k_s$ is the core surface rate for ionic exchange, and $D_e$ is the effective diffusivity of the cation.

The fraction of protein release, θ, assuming that the process is controlled by the particle swelling occurring in the above presented shell-progressive form, is given by $$\theta = 1 - \left(\frac{r_c}{R}\right)^3 \quad (4)$$

Equations (1)-(4) can be combined to obtain $$\frac{d\theta}{dt'} = \frac{N_s C_l'}{\frac{1}{Sh} + \frac{1 - r_{c/R}}{\tau_{c/R}} + \frac{1}{Da(\tau_{c/R})^2}} \quad (5)$$

where the dimensionless groups are $$Sh = k_l R / D_e \quad \text{(Sherwood number)}$$
$$Da = k_s R / D_e \quad \text{(Damköhler number)}$$
$$N_s = 3 D_e t_r C_{lr} / R^2 \rho_s C_\infty$$
$$t' = \frac{t}{t_r} \text{ and } C_l' = \frac{C_l}{C_{lr}}$$

Where $t_r$ and $C_{lr}$ are reference time and concentration values. The Sherwood number represents the ratio of the external interfacial mass transfer to the rate of intraparticle diffusion. The Damköhler number relates the ionic exchange time scale with the intraparticle diffusion rate. Equation (5) can be solved for the case of constant bulk fluid concentration, $C_l$, giving an implicit solution for θ

$$\tau = \frac{1}{3}\left(\frac{1}{Sh} - 1\right)\theta - \frac{1}{2}[1-\theta]^{2/3} + \frac{1}{2} - \frac{1}{Da}[1-\theta]^{1/3} + \frac{1}{Da} \quad (6)$$

with the dimensionless time $$\tau = \frac{1}{3} N_s t' C_l' \quad (7)$$

Equation (6) can be used to simulate the protein release profile. The most common approach found in the literature to obtain the kinetic parameters is from the slope of the straight line fitting the initial data (θ<0.6) of θ vs $t^{0.5}$).[5] However, it was noticed that the release of proteins from RPS may have a sigmoidal shape when plotted as θ versus $t^{0.5}$. Equation (6) is more general; it includes additional mass transport resistances that contribute for the sigmoidal shape of the protein release profiles.

In an embodiment, the RPS produced by *Cyanothece* sp. CCY 0110 may be use for the microencapsulation of the vitamin B12 and its controlled release. The vitamins are important micronutritional compounds which are involved in many biochemical functions in the human body but are not endogenously produced, needing to be supplied through diet. Vitamin B12 is the most chemically complex and largest of all the vitamins and is involved in cell metabolism (DNA synthesis and regulation), in the normal operation of the brain and nervous system, and in the formation of blood. Microencapsulation can minimize the factors that interfere with the stability of the vitamins and allow the controlled release, increasing their applicability in food and pharmaceutical processes.

In an embodiment, the apparent viscosity of the RPS produced by *Cyanothece* sp. CCY 0110 was measured over a range of different shear rates. Aqueous solutions of 0.1%, 0.5% and 1.0% (w/v) revealed a rheological behaviour typical of non-Newtonian fluids with pseudoplastic behaviour or shear thinning properties in aqueous solutions.

In an embodiment, the emulsifying property of the RPS produced by *Cyanothece* sp. CCY 0110 was studied. Aqueous solutions of 0.1%, 0.5% and 1.0% (w/v) were able to form detectable emulsions in the presence of n-hexane, liquid paraffin and vegetable oil, with emulsification indexes equal or above 50% and stable over a month.

In an embodiment, the RPS was compared with xanthan gum commercially available in terms of viscosity and emulsifying properties, revealing a similar behaviour typical from good bioemulsifiers. This knowledge is important in food industry, for providing good sensory qualities, flavour release and suspending properties, and in cosmetic industry, for the production of lotions, creams and gels.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above-described embodiments are combinable.

The following claims further set out particular embodiments of the disclosure.

The following references, should be considered herewith incorporated in their entirety:

1. Appel E A, Loh X J, Jones S T, Dreiss C A, Scherman O A. 2012. Sustained release of proteins from high water content supramolecular polymer hydrogels. Biomaterials 33(18):4646-52.
2. Ahmed T A, Aljaeid B M. 2016. Preparation, characterization, and potential application of chitosan, chitosan derivatives, and chitosan metal nanoparticles in pharmaceutical drug delivery. Drug Design, Development and Therapy 10:483-507.
3. Pereira S, Zille A, Micheletti E, Moradas-Ferreira P, De Philippis R, Tamagnini P. 2009. Complexity of cyanobacterial exopolysaccharides: Composition, structures, inducing factors and putative genes involved in their biosynthesis and assembly. FEMS Microbiology Reviews 33(5):917-941.
4. Mota R, Guimarães R, Büttel Z, Rossi F, Colica G, Silva C, Santos C, Gales L, Zille A. De Philippis R and others. 2013. Production and characterization of extracellular carbohydrate polymer from *Cyonothece* sp. CCY 0110. Carbohydrate Polymers 92(2):1408-1415.
5. Koutsopoulos S, Unsworth L D, Nagai Y, Zhang S. 2009. Controlled release of functional proteins through designer self-assembling peptide nanofiber hydrogel scaffold. Proceedings of the National Academy of Sciences 106(12): 4623-4628.

The invention claimed is:

1. A method for providing controlled drug delivery to a wound in a subject, which comprises:
    administering to the subject a pharmaceutical composition comprising a polysaccharide released from Cyanothece sp. CCY 0110, and
    an active ingredient selected from the group consisting of: a protein, a drug, an anti-inflammatory agent, an antiseptic agent, an antipyretic agent, an anaesthetic agent, an anti-cancer agent, a therapeutic agent, and a mixture thereof.

2. The method of claim 1, wherein the polysaccharide comprises a residue selected from the group consisting of: mannose, glucose, galactose, xylose, arabinose, rhamnose, fucose, galacturonic acid, glucuronic acid, and a peptide.

3. The method of claim 2, wherein the polysaccharide further comprises a divalent cation selected from the group consisting of: $Ba^{2+}$, $Fe^{2+}$, $Ca^{2+}$, $Cu^{2+}$, $Zn^{2+}$, and mixtures thereof.

4. The method of claim 1, wherein the weight of the polysaccharide is between 1500 and 5000 KDa.

5. The method of claim 1, wherein the pharmaceutical composition is administered topically, parenterally or orally to the subject.

6. The method of claim 5, wherein the pharmaceutical composition is administered to the subject once a day, twice a day, or three times a day.

7. The method of claim 1 comprising 0.01-2% (w/v) of the polysaccharide.

8. The method of claim 7 comprising 0.05-1% (w/v) of the polysaccharide.

9. The method of claim 8 comprising 0.1-0.5% (w/v) of the polysaccharide.

10. The method of claim 1, wherein the pharmaceutical composition comprises an additional polysaccharide selected from the group consisting of: cellulose, alginate, chitosan, gellan gum, arabic gum, dextrin, dextran, guar gum, carrageenan, xanthan gum, hyaluronic acid, and a mixture thereof.

11. The method of claim 1, wherein the pharmaceutical composition is a gel, a cream, or a lotion.

12. The method of claim 1 further comprising a hydrogel selected from the group consisting of: hyaluronic acid, dextran, alginate, collagen, gellan gum, and a mixture thereof.

* * * * *